United States Patent [19]

Lindsay et al.

[11] 4,279,774

[45] Jul. 21, 1981

[54] METHOD OF REMOVING LIPID INHIBITORS FROM LIMULUS AMEBOCYTE LYSATE

[75] Inventors: Gene K. Lindsay, Middletown; Andrew J. O'Beirne, Walkersville, both of Md.

[73] Assignee: Dynasciences Corporation, Los Angeles, Calif.

[21] Appl. No.: 93,403

[22] Filed: Nov. 13, 1979

[51] Int. Cl.$^3$ .................. G01N 31/00; G01N 21/04; G01N 33/48
[52] U.S. Cl. .................. 252/408; 23/230 B; 210/634; 424/12; 424/95; 424/101; 435/34; 435/38; 435/259
[58] Field of Search ............ 23/230 B; 252/408; 424/101, 12, 95; 210/22 R, 21; 435/34, 38, 259

[56] References Cited

U.S. PATENT DOCUMENTS

| | | | |
|---|---|---|---|
| 2,094,931 | 10/1937 | Schultze | 424/101 |
| 3,915,805 | 10/1975 | Levin | 23/230 B |
| 4,038,029 | 7/1977 | Teller et al. | 23/230 B |
| 4,056,468 | 11/1977 | Breiter et al. | 23/230 B |
| 4,096,091 | 6/1978 | Hopkins | 252/408 |
| 4,107,077 | 8/1978 | Sullivan et al. | 252/408 |

*Primary Examiner*—Teddy S. Gron
*Attorney, Agent, or Firm*—Donald E. Nist

[57] ABSTRACT

The improved method of the present invention involves the removal of lipid inhibitors from Limulus amebocyte lysate to increase the sensitivity and quality of the lysate. The method comprises intimately contacting, as by mixing and stirring, Limulus amebocyte lysate with a selected binary liquid solvent system for a time sufficient to draw water into the solvent system from the lysate and to effectively extract and denature the lipid inhibitors in the lysate. The ability of the binary solvent to draw in water from the lysate and form, in effect, a new tertiary system is the important factor in this methodology. The amount of water drawn into the solvent is controlled by the amount of polar solvent in the solvent system. After this extraction and denaturation, the lysate is then separated from the solvent system and recovered in purified form of increased sensitivity.

15 Claims, No Drawings

METHOD OF REMOVING LIPID INHIBITORS FROM LIMULUS AMEBOCYTE LYSATE

BACKGROUND OF THE INVENTION

1. Field of the Invention

The present invention generally relates to Limulus amebocyte lysate and more particularly to an improved method of removing suspected lipid inhibitors from the lysate.

2. Prior Art

Bacterial endotoxins are lipopolysaccharides associated with the outer membrane of gram negative bacteria. Various means for detecting the endotoxins have been devised. One of the newer test methods involves the use of lysate isolated from the amebocytes of the horseshoe crab, Limulus polyphemus. This method is very sensitive, that is, it can detect low level concentrations of the endotoxin in both aqueous samples such as pharmaceuticals and in human body fluids such as blood serum.

The lysate is obtained by osmotically bursting or otherwise breaking the cell wall of the amebocytes once they have been isolated from the blood of the crab, and separating out the cell wall debris. A positive test for the presence of Gram-negative bacterial infection (i.e. the presence of endotoxins in the blood sample) is gelation of the lysate within a reasonable amount of time after mixing it with the blood serum sample. Before this test is performed, the pH of the sample must be adjusted and any specific inhibitors to the gelation must be removed. Blood serum samples for instance must first be purified, as by chloroform extraction or the like, to remove gelation inhibitors from the blood. It has been found that, unfortunately, the sensitivity of the lysate seems to differ from batch to batch. It is now believed that certain natural lipids in the lysate are responsible for inhibiting or blocking the endotoxin gelation reaction. Removal of such lipid inhibitors increases the sensitivity of the lysate.

U.S. Pat. No. 4,107,077 to Sullivan and Watson deals with a method of removing such lipid inhibitors by extracting the lysate with a single organic solvent selected from the group consisting of chloroform, iodoform, bromoform, methyl bromide, methyl chloride, methyl iodide, ethyl chloride, ethyl bromide, ethyl iodide, propyl chloride, propyl bromide, propyl iodide, ethylene chloride, methylene chloride, chlorobenzene, bromobenzene, iodobenzene, dimethyl ether, diethyl ether, carbon tetrachloride, trichloroethylene, toluene and hexane. Chloroform is the solvent which this patent points to as having the greatest utility in this procedure. The procedure involves mixing the single solvent, such as chloroform, with two or more parts of the lysate, stirring gently for about an hour and then separating the lysate from the chloroform. While greatly improved lysate of greater uniformity is obtained by this procedure, unfortunately very little control is exercised by the procedure over the amount of protein in the lysate which is denatured, along with the inhibitor, by the solvent. Good, though not optimal, results are obtained but only with a very few solvents which exhibit a desirable degree of extractability.

It would be desirable to be able to provide an improved method of removing lipid inhibitors from Limulus amebocyte lysate which method could be optimized to denature the lipid inhibitors without adversely affecting the proteins in the lysate so as to improve the sensitivity and uniformity of the lysate to a greater degree than heretofore possible, regardless of the initial quality of the lysate. It would also be desirable to provide an improved method which would reduce the amount of solvent required to effect full and proper extraction and denaturation and/or reduce the total extraction and denaturation time.

SUMMARY OF THE INVENTION

The present invention satisfies all of the foregoing needs. The invention is substantially as set forth in the Abstract above and comprises an improved method of removing lipid inhibitors from Limulus amebocyte lysate to provide lysate of increased sensitivity and quality.

The method is simple, more rapid, with better results using economical binary solvents. It involves intimately contacting Limulus amebocyte lysate with a selected binary liquid solvent system for a time sufficient to effectively extract and denature lipid inhibitors in the lysate without adversely affecting proteins in the lysate. The lysate is then separated from the solvent system and recovered in purified form.

The solvent system comprises first and second selected organic solvents, the solvents differing from each other in polarities. One of the solvents is a solvent of high polarity while the other solvent is of either low polarity or is essentially non-polar. The solvent of low polarity or non-polarity is present in a major concentration in the system while the high polarity solvent is present in a minor concentration, not in excess of about 10–25 volume percent and preferably not in excess of about 2–5 volume percent. The non-polar solvent or solvent of low polarity preferably is an aromatic such as benzene or toluene or a halogenated, preferably chlorinated, paraffin such as trichloroethane. Paraffins, such as hexane and pentane can also be used, as well as cycloparaffins such as cyclohexane and cyclopentane. The non-polar solvent preferably is selected from the group consisting of benzene, toluene and trichloroethane. A mixture of compatible non-polar solvents such as toluene plus benzene can be used as the first solvent, if desired.

The solvent of high polarity in the system preferably comprises one or a mixture of low molecular weight alcohols selected from the group consisting of methanol, ethanol and propanol. However, other single alcohols or mixtures of alcohols such as isopropanol, isobutanols and the like can be used. Preferred binary solvent systems include benzene plus methanol, toluene plus ethanol, trichloroethane plus propanol, benzene plus ethanol and trichloroethane plus ethanol. Toluene plus ethanol is the most preferred system. Further details are set forth in the following specific description.

DETAILED DESCRIPTION

In accordance with the method of the present invention, Limulus amebocyte lysate is contacted with a selected binary liquid solvent system in an effective concentration and for a time sufficient to perform the desired functions of drawing water into the system from the lysate and extracting and effectively denaturing the lipid inhibitors in the lysate.

It is to be noted that the concentration of the polar solvent should be, as previously indicated, not in excess of about 10–25 volume percent, concentrations of about 2–5 volume percent being preferred. The Limulus amebocyte lysate upon which the extraction-denaturation is carried out by the binary solvent system is one which is commercially available and is well described in the aforesaid Sullivan-Watson patent and elsewhere. Typically, the lysate is prepared by heart bleeding of horseshoe crabs, collecting and pooling the collected blood, separation of the amebocytes from the remainder of the blood by centrifugation or the like, followed by washing and then lysing the amebocytes, as by crushing the cells and centrifuging the cell debris from the lysate. Other methods of lysing have also been described in the literature.

In accordance with the present method the lysate is intimately contacted with the binary solvent (volume ratio of solvent-to-lysate, about 1:2), as by mixing and gently stirring the lysate and solvent system together at intervals over a suitable contact period, for example about one-half hour, at ambient temperature or the like, preferably about 60° F.–70° F. At the end of this treatment time, the lysate is separated from the solvent system, by careful decanting and then gravity centrifugation at about 500xg for about 30 minutes. The solvent mixture is in the bottom or top portion of the centrifuge tube, depending on the particular solvent system used. The solvent system is then separated from the lysate and is recovered. Preferably, the lysate is lyophilized to place it in a readily storable state. Lyophilization can be carried out by any standard procedure, for example, the lysate can be frozen at about $-60°$ C. or the like and can be subjected to a suitable low vacuum in the frozen state to draw off the moisture and liquid, leaving the purified lystate in dry powder from which can then be sealed under vacuum, for storage. The lysate can then be readily reconstituted in sterile pyrogen-free water for use in the endotoxin detection test.

The following specific examples illustrate certain features of the present invention:

EXAMPLE I

Two batches of Limulus amebocyte lysate [batches A and B] were prepared in accordance with the following procedure:

Horseshoe crabs were obtained from the Central Atlantic coastal area, specifically from off the coast of Maryland and Virginia. The crabs were bled two or four times a week, averagaing about 700 ml of blood per week. After bleeding, the crabs were retured to the ocean. Lysate was prepared from the collected blood as follows:

1. 200 ml of blue blood, containing amebocytes, was bled directly from the crab into a 50 ml aqueous solution containing 0.125% N-ethylmaleimide and 3.0% NaCl.
2. This mixture was centrifuged to concentrate the amebocytes. The supernatant blue blood was decanted and discarded.
3. The amebocytes were resuspended in a 3.0% NaCl aqueous solution to a final volume just under 50 ml. This solution was transferred to a 50 ml centrifuge tube and again centrifuged to collect the cells. The supernatant solution was discarded.
4. The white amebocytes were again resuspended in a 3.0% NaCl aqueous solution to a final volume just under 50 ml. The mixture was again centrifuged to collect the amebocytes and the supernatant solution descarded.
5. The volume of the white amebocyte cell pack was estimated and distilled water added to 3 to 5 times the cell volume. The cells were resuspended and the total contents poured into a large glass flask held at 4° C. on wet ice.
6. As many as 50 of these small tubes were combined in the glass container during the course of a bleeding day. At the end of each bleeding day, the flask and its contents of amebocyte cells and distilled water was placed on a shaking table at 4° C. and allowed to swirl gently overnight.
7. The next day (or about 20 hours later), the limulus amebocyte lysate was decanted from the burst cell contents and the lysate stored at $-70°$ C. in 500 ml volumes.
8. When finished LAL was needed, the frozen lysate was thawed and mixed with one-half its volume of binary solvent in accordance with the present method or with a test solvent.
9. The extracted lysate was decanted from the binary solvent and then salts were added to a final concentration of 0.9% NaCl and 0.2% $CaCl_2$. The lysate was now ready to clarify by centrifugation and to be lyophilized in 50 ml bulk quantities.
10. After lyophilization, the lysate was ready to use for finished vialing or extended storage at $-20°$ C.

Batch A was extracted with chloroform [1 volume of chloroform to 2 volumes of the Limulus amebocyte lysate], the extraction taking place for a half-hour at 2 to 8° C. with gentle manual stirring of the mixture of the Limulus amebocyte lysate and the chloroform. The treated Limulus amebocyte lysate was then allowed to settle, the chloroform was then decanted from the Limulus amebocyte lysate, after which salts were added to final concentration of 0.9% of NaCl and 0.2% $CaCl_2$. Then the lysate was centrifuged at about 500xg for about 30 minutes, separated from the residual chloroform and then lyophilized in 1.0 milliliter volumes. The same procedure was utilized on batch B except that batch B was extracted with 1 volume of benzene containing 5 percent by volume of ethanol to 2 volumes of the Limulus amebocyte lysate, in place of the chloroform.

The following day, the lyophilized lysate in each case was reconstituted to original volumes of 1.0 milliliter in pyrogen-free distilled water. Each aliquot so reconstituted was then reacted with E. Coli endotoxin preparation known to rect with the same sensitivity as the FDA National Standard Endotoxin known as EC2. The lysate aliquots known to have been extracted with the chloroform [batch A aliquots] were found to have a sensitivity of 0.125 ng/ml of endotoxin. The lysate extracted with the binary solvent mixture of benzene and ethanol exhibited a sensitivity of 0.062 ng/ml, demonstrating that batch B extracted with the binary solvent system was twice as sensitive as the chloroform-extracted batch A in parallel tests. In addition to it being more sensitive, the binary solvent system-extracted lysate had greater clarity and reconstituted more rapidly than the lysate extracted with chloroform.

In carrying out the testing, all aliquots of the lysate had salts added to them in an amount to yield 0.02 M calcium chloride and 0.0154 M sodium chloride before the testing. The testing for endotoxin sensitivity was performed by the recognized FDA approved method of combining 0.1 ml sample of the endotoxin and 0.1 ml of the lysate in a 10×75 mm tube and incubating the mixture at 37° C. for one hour. A positive test was interpreted to be that where a gel formed which remained intact when the tube was inverted 180°. A negative test was one in which no gel formed in which the gel did not remain intact during the inversion. The sensitivity of the lysate was determined by running the test with parallel aliquots using a two-fold series of dilutions of the standard endotoxin with the lysate and assigning the value of the greatest dilution to give a positive test to the lysate. Thus, the endotoxin was tested at 1.0 ng/ml, and also diluted to one-half, one-quarter and one-eighth of that strength etc., the dilutions being listed as 1, 0.5, 0.25, 0.125, (in ng/ml).

The improved results obtained by a typical binary solvent system in accordance with the present method over a single solvent such as chloroform are amply demonstrated in this example.

EXAMPLE II

The procedure of Example I was carried out on the following batches utilizing the extraction solvents as listed in Table 1 below:

TABLE 1

| Lysate Batch | Extracting Solvent(s) | Sensitivity of Lysate |
|---|---|---|
| C | Chloroform | 0.50 ng/ml |
|  | Chloroform + 1% ethanol (by volume) | 0.50 ng/ml |
|  | Chloroform + 5% ethanol | 0.25 ng/ml |
| D | Benzene | 1.0 ng/ml |
|  | Benzene + 2% methanol | 0.25 ng/ml |
|  | Benzene + 5% methanol | 0.25 ng/ml |
|  | Benzene + 10% methanol | 0.50 ng/ml |
|  | Benzene + 25% methanol | 1.0 ng/ml |
|  | Benzene | 1.0 ng/ml |
|  | Benzene + 2% ethanol | 0.125 ng/ml |
|  | Benzene + 5% ethanol | 0.125 ng/ml |
|  | Benzene + 10% ethanol | 0.50 ng/ml |
|  | Benzene + 25% ethanol | 0.50 ng/ml |
| E | Trichloroethane | 1.0 ng/ml |
|  | Trichloroethane + 2% ethanol | 0.125 ng/ml |
|  | Trichloroethane + 5% ethanol | 0.125 ng/ml |
|  | Trichloroethane + 10% ethanol | 0.250 ng/ml |
|  | Toluene | 0.5 ng/ml |
|  | Toluene + 2% ethanol | 0.125 ng/ml |
|  | Toluene + 5% ethanol | 0.125 ng/ml |
|  | Toluene + 10% ethanol | 0.250 ng/ml |
|  | Trichloroethane | 1.0 ng/ml |
|  | Trichloroethane + 2% propanol | 0.250 ng/ml |
|  | Trichloroethane + 5% propanol | 0.125 ng/ml |
|  | Trichloroethane + 10% propanol | 0.250 ng/ml |

Table 1 above indicates that far better results are obtained with a binary solvent system then any single solvent tested. Results showing as great a sensitivity as 0.125 ng/ml are obtained with 2-5% ethanol is benzene, trichloroethane or toluene and 5% propanol in trichloroethane.

Examples I and II clearly demonstrate the desirability of the binary solvent system in the method of the present invention to purify and sensitize Limulus amebocyte lysate, optimizing the solvent to denature only the desired components without materially affecting any other components.

In this specification and in the claims by highly polar solvent is meant a solvent which would register at least about 0.8 on the elutotrophic series scale originally disclosed in an article in the Journal of Chromatography, Volume 16, page 55 (1964) and also appearing in a book entitled: Chromatography, second edition, pages 59-60, edited by E. Heftmann. By solvent of low polarity is meant a solvent which would register not more than about 0.5 on the elutotrophic series scale. By nonpolar solvent is meant a solvent which would register 0 or near 0 on the elutotrophic series scale.

Various changes and modifications, alterations and additions can be made in the method of the present invention, its steps and parameters. All such changes, alterations, modifications and additions as are within the scope of the appended claims form part of the present invention.

What is claimed is:

1. An improved method of removing lipid inhibitors from Limulus amebocyte lysate to increase the sensitivity and quality of the lysate, said method comprising:

(a) intimately contacting Limulus amebocyte lysate with a selected binary liquid solvent system containing first and second selected organic solvents of differing polarities, said first solvent being of low polarity registering not in excess of about 0.5 on the elutotrophic series scale, said second solvent being of high polarity registering at least about 0.8 on said elutotrophic series scale, said second solvent being present in said solvent system in a concentration of about 2–25% by volume of said system, said solvents being present in an amount and contacting said lysate for a time sufficient to draw water into said solvent system from said lysate and extract and denature lipid inhibitors in said lysate; and, (b) separating said Limulus amebocyte lysate and said solvent system from each other and recovering said lysate in purified form having improved sensitivity.

2. The improved method of claim 1 wherein said system is used in a volume ratio of about 1:2 to said lysate.

3. The improved method of claim 1 wherein said first solvent is an aromatic and said second solvent is a low molecular weight alcohol.

4. The improved method of claim 3 wherein said system comprises a major concentration of benzene and a minor concentration of methanol.

5. The improved method of claim 4 wherein said methanol is in a concentration of about 2–5 volume per cent in said system.

6. The improved method of claim 3 wherein said system comprises benzene and ethanol.

7. The improved method of claim 6 wherein said ethanol is present in said system in a concentration of about 2–5 volume percent.

8. The improved method of claim 3 wherein said system comprises toluene and a low molecular weight alcohol.

9. The improved method of claim 8 wherein said alcohol comprises methanol in a concentration of about 2–5 volume percent in said system.

10. The improved method of claim 8 wherein said alcohol comprises ethanol in a concentration of about 2–5 volume percent in said system.

11. The improved method of claim 1 wherein said system comprises a multi-halogenated paraffin and a low molecular weight alcohol.

12. The improved method of claim 11 wherein said system comprises trichloroethane and ethanol, the latter in a concentration of about 2–5 volume percent in said system.

13. The improved method of claim 11 wherein said system comprises trichloroethane and propanol, the latter in a concentration of about 2–5 volume percent in said system.

14. The improved method of claim 1 wherein said contacting is effected by mixing said lysate with said system for approximately one-half hour, and wherein said separating is effected by decanting said system from said lysate, whereupon said lysate is lyophilized.

15. The improved method of claim 1 wherein said first solvent is selected from the group consisting of benzene, trichloroethane and toluene, and mixtures thereof, and wherein said second solvent is selected from the group consisting of methanol, ethanol and propanol, and mixtures thereof.

* * * * *